United States Patent
Nimberger

Patent Number: 5,109,709
Date of Patent: May 5, 1992

[54] DIRECT MOUNT SYSTEM FOR A FLUID SAMPLING PUMP AND METHOD

[76] Inventor: Spencer M. Nimberger, 13711 Chelwood Pl., Houston, Tex. 77069

[21] Appl. No.: 586,499

[22] Filed: Sep. 21, 1990

Related U.S. Application Data

[63] Continuation-in-part of Ser. No. 496,368, Mar. 19, 1990.

[51] Int. Cl.⁵ .............................................. G01N 1/14
[52] U.S. Cl. .................................................. 73/863.84
[58] Field of Search ........... 73/863.83, 863.84, 864.34, 73/866.5, 201

[56] References Cited

U.S. PATENT DOCUMENTS

4,391,152  7/1983  Ellet ................................. 73/863.84

Primary Examiner—Robert Raevis
Attorney, Agent, or Firm—Browning, Bushman Anderson & Brookhart

[57] ABSTRACT

An interface is provided for mounting a sampling pump to a flow line. The sampling pump includes a pump manifold having a hot loop flow path through the manifold, and the pump has an inlet along the hot loop. The interface includes an interface body having tapered threads at a lower end thereof for sealing engagement with the threads of a flow line nipple, first and second fittings, first and second nipples for sealing engagement with ports in the pump manifold body, a spacer nipple, and an interface plate for mounting between the interface body and the pump manifold. The interface of the present invention may be used to mount or remount a pump and related components within an enclosure to a flow line, and the rotational position of the enclosure may be selected after the pump body has been threaded to the flow line nipple. A method is disclosed for efficiently mounting the pump to the flow line, thereby substantially reducing installation costs.

18 Claims, 3 Drawing Sheets

DIRECT MOUNT SYSTEM FOR A FLUID SAMPLING PUMP AND METHOD

RELATED CASES

The present application is a continuation-in-part of U.S. Application Ser. No. 07/496,368 filed Mar. 19, 1990.

BACKGROUND OF THE INVENTION

1. Field of the Invention

The present invention relates to sampling pumps of the type commonly used to intermittently withdraw sample hydrocarbon fluids from a pipeline and input those fluids to a sample vessel for subsequent analysis, and more particularly relates to improved techniques for mounting the sample pump and related equipment directly to the pipeline.

2. Description of the Background

Sampling pumps have been used for years to intermittently withdraw fluid samples from a hydrocarbon pipeline and input those samples to a suitable container for subsequent analysis. The price charged for hydrocarbons being transmitted through the pipeline is typically determined as a function of (a) the volume of the actual fluid transferred through the pipeline, and (b) the BTU content of sample fluid intermittently withdrawn from the pipeline. The sample fluid vessel is periodically transported to a laboratory for fluid analysis by any suitable instrument, such as a gas chromatograph. The accuracy of the sampling technique, i.e., the caloric or BTU value of the fluid sample in the vessel compared to the average BTU value of all the fluid transmitted through that pipeline, thus has a significant affect on the price paid for the transmitted fluid. Accordingly numerous attempts have been made and will continue to increase the reliability and accuracy of this sampling technique, while at the same time lowering the overall sampling costs One version of a sampling pump is disclosed in U.S. Pat. No. 4,403,518. U.S. Pat. No. 4,470,773 discloses a similar pump with a feature for breaking the vacuum in the pump which could otherwise be created by the retraction of the collection probe from the resilient plug. The prime mover for reciprocating the sampling pump piston is typically a diaphragm, which in turn is powered by a pressurized air source, as disclosed in U.S. Pat. Nos. 4,440,032 and 4,525,127. U.S. Pat. No. 4,557,157 discloses a sampling pump which also utilizes this type of prime mover, and further discloses a pressure balanced check valve external of the pump body. This check valve utilizes line pressure as a reference, and enables the pump to perform its desired function of transmitting a preselected fluid volume per stroke regardless of line pressure.

Most sampling pumps are primarily intended to pump either a liquid or a gas, but not both. A representative liquid sampling pump is disclosed in U.S. Pat. No. 4,172,670, while a gas sampling pump is described in U.S. Pat. No. 4,531,895. A combined pump and sample vessel is disclosed in U.S. Pat. No. 4,628,750. Operators of sampling pumps frequently prefer a "hot loop" between the pipeline and the pump. The hot loop flows a slight amount of fluid continuously from the pipeline to the generally vicinity of the pump, so that the pump is sampling fluid reasonably respresentative of the fluid flowing through the pipeline at each sampling period. If the hot loop is not provided, fluid is drawn with each pump stroke into the flow line between the pipeline and the sampling pump, but the pump is then transmitting fluid into the sample container from previous pump strokes, which inherently reduces the accuracy of the sampling technique. In the hot loop system, fluid which is not sampled may be returned to the pipeline.

It is conventional to house the sampling pump, the pump actuator, a regulator, and an electronic sampling controller within a single protective housing, and then connect ports extending from the housing to the pipeline by flexible tubing. The protective housing is thus generally mounted separate from the pipeline. Fluid sampling pump manufacturers have recently promoted systems which mount the pump directly to the pipeline, thereby reducing installation cost. Previous direct mounting systems for sampling pump have significant disadvantages, however, which have reduced their commercial acceptance. While a new pump and manifold assembly may be manufactured and sent to the field to allow direct mounting of the pump to the pipeline via the manifold, such a system does not practically benefit an operator with an existing conventional sampling pump housed within a protective enclosure with related equipment, since the existing pump has to be disconnected from the related equipment and effectively removed from the enclosure to install the new manifold on the pump, then the assembly has to be reconnected and remounted within the enclosure so that the pump within the enclosure is now directly mounted to the pipeline. The cost and time associated with such disconnection, disassembly, and reconnection operations typically does not justify the benefit obtained by direct mounting of the pump, especially since some provisions previously had to made to support the pump and enclosure separate from the pipeline.

Another disadvantage of existing systems directly connecting a pump to a pipeline is that the manifold is rotatably fixed to the pump prior to shipping the assembly to the field for installation, and the rotatable position of the installed manifold is uncontrollably determined by the tapered threads which connect the manifold to the pipeline nipple. Tapered or NPT threads should be "made up" within a certain torque range and neither under torqued (which may result in fluid leakage) or over torqued, which could cause fracture of the tapered threads in the manifold or the mating threads on the nipple. Since the pump is rotatably fixed to the manifold, the rotational position of the pump is determined by the tapered threads, and the position of manifold cannot be effectively predetermined. The operator in the field, however, almost always prefers that the face of the pump and/or the face of the enclosure housing the pump and related equipment be at a certain position, so that the controller within the enclosure can be easily adjusted and the components within the enclosure checked. Accordingly, installation personnel tend to over-tighten the tapered threads between the manifold and the pipeline nipple to force the enclosure face to be at the desired orientation. This over-tightening can cause failure which may not occur at the time of the installation, and accordingly the installed system may first begin to leak or rupture months after installation due to over tightening of the manifold threads to the pipeline nipple.

The disadvantages of the prior art are overcome by the present invention, and an improved sampling pump and direct mount system for a sampling pump is hereinafter disclosed. The pump of the present invention is suitable for reliably withdrawing various sample fluids from a pipeline at various line pressures and inputting those fluids to a desired sample vessel. The direct mount system enhances the versatility of the sampling procedure, reduces installation costs, minimizes maintainance, and may be easily adapted to existing systems.

SUMMARY OF THE INVENTION

A sampling pump is provided with a large diameter piston capable of pumping a discrete yet small volume of gas during each piston stroke. The stroke of the piston is readily adjustable, and the same sampling pump is capable of pumping a correspondingly discrete yet significantly larger quantity of fluid during the adjusted longer stroke. Accordingly, both manufacturing and servicing costs can be reduced according to the present invention, since one pump may more frequently be utilized for pumping either various gases or various liquids from respective pipelines to their associated sample vessels.

An interface is used interconnect the pump and pump manifold assembly to the pipeline. The pump, pump manifold, and related equipment may be housed within an enclosure, with interface nipples extending through the enclosure to seal with the pump manifold. The interface assembly transmits fluid from the pipeline to one of the nipples and from the other nipple back to the pipeline in a hot loop, and provides a structural direct mounting for supporting the pump, the enclosure, the related equipment within the enclosure, and any equipment secured to the enclosure, such as a solar module. The interface assembly includes a first valve for selectively terminating or permitting fluid flow in the hot loop to the pump, and a second valve for selectively terminating flow in the hot loop from the pump back to the flow line.

The interface assembly includes a main interface body with a pair of internal flow paths and a mounting plate positioned between the pump manifold and the interface body. First and second fluid flow fittings are sealed to the plate, and corresponding first and second nipples interconnect the ports in the pump manifold to the fittings and thus the plate. The plate is sealed to a face of the interface body, and bolts structurally interconnect the body and plate. The first and second nipples provide structural support between the plate and the pump manifold in a direction passing through the axes of the nipples, and a pair of special bolts whose axes lies within an opposing plane provide structural support between the plate and the manifold to substantially increase structural integrity of the system.

The interface assembly may be installed so that the nipples extending through the enclosure, and the installation completed without disconnecting the pump from related equipment within the enclosure or removing the pump from the enclosure. Conventional fluid flow lines between the pipeline and each of these nipples is obtained, and the enclosure with the pump and manifold internal thereof efficiently secured to the interface, with the interface secured to the pipeline.

The interface body includes tapered threads for connecting to mating threads on a pipeline nipple. These threads can be made up to their desired torque, and the pump and enclosure thereafter rotatably moved with respect to the interface body to a desired rotation which positions the face of the pump or the enclosure at the position selected by the operator. After the plate is fixed to the pump manifold by the nipples, the plate and enclosure assembly may be rotated with respect to the interface body, and the bolt holes in the interface body selectively aligned with threaded holes in the plate for securing the plate to the body at the desired rotational position. During rotation of the plate and assembly within the enclosure with respect to the interface body, the heads of the fittings rotate within a circular groove provided in the face of the interface body, with the groove also providing the fluid connection between one fitting and the return hot loop passageway through the interface body.

It is an object of the present invention to provide an improved pump capable of pumping discrete quantities of either a liquid or a gas from either a flow line or storage vessel into a sample vessel, or from a container vessel into a flow line.

It is an object of the present invention to provide a pump capable of displacing a small volume of a compressible gas utilizing a relatively short pump stroke, while also providing a relatively large diameter piston movable within the pump bore to displace a large quantity of liquid.

It is an object of this invention to provide a direct mounting system for mounting a sampling pump to a pipeline which allows an existing pump and pump manifold within an enclosure to be mounted to the pipeline without disconnecting the pump from related equipment within the enclosure.

It is another object of the present invention to provide a direct pumping system for interconnecting a sampling pump with a pipeline which allows the sampling pump and/or enclosure which houses the sampling pump to be rotated at a desired position after the interface body has been rotatably fixed to the pipeline.

It is a feature of the present invention that the same mounting interface may be used to mount a new sampling pump to a pipeline in a new installation, or to easily remount an existing sampling pump to a pipeline in a revised installation.

It is a further feature of the present invention that the interface body may be rotatably fixed to a pipeline nipple and the pump interconnected to the interface body thereafter rotated with respect to the body, so that the installer does not tend to overtorque the body to the pipeline in order to position the pump at a desired orientation.

It is an advantage of the present invention that the flow paths between the pipeline and the sampling pump are significantly reduced, thereby minimizing maintenance costs for the system.

It is a further advantage of the invention that a sampling pump and its related equipment may be easily mounted to the pipeline without additional support, thereby substantially minimizing installation time and expense.

It is yet a further advantage of the invention that the pump is provided with a manifold connected directly to the pump body at a location adjacent the pump inlet port, thus minimizing the distance between the hot loop passageway and the inlet check valve for the pump.

These and further objects, features, and advantages of the present invention will become apparent from the following detailed description, wherein reference is made to the figures in the accompanying drawings.

DETAILED DESCRIPTION OF PREFERRED EMBODIMENTS

Figure 1:
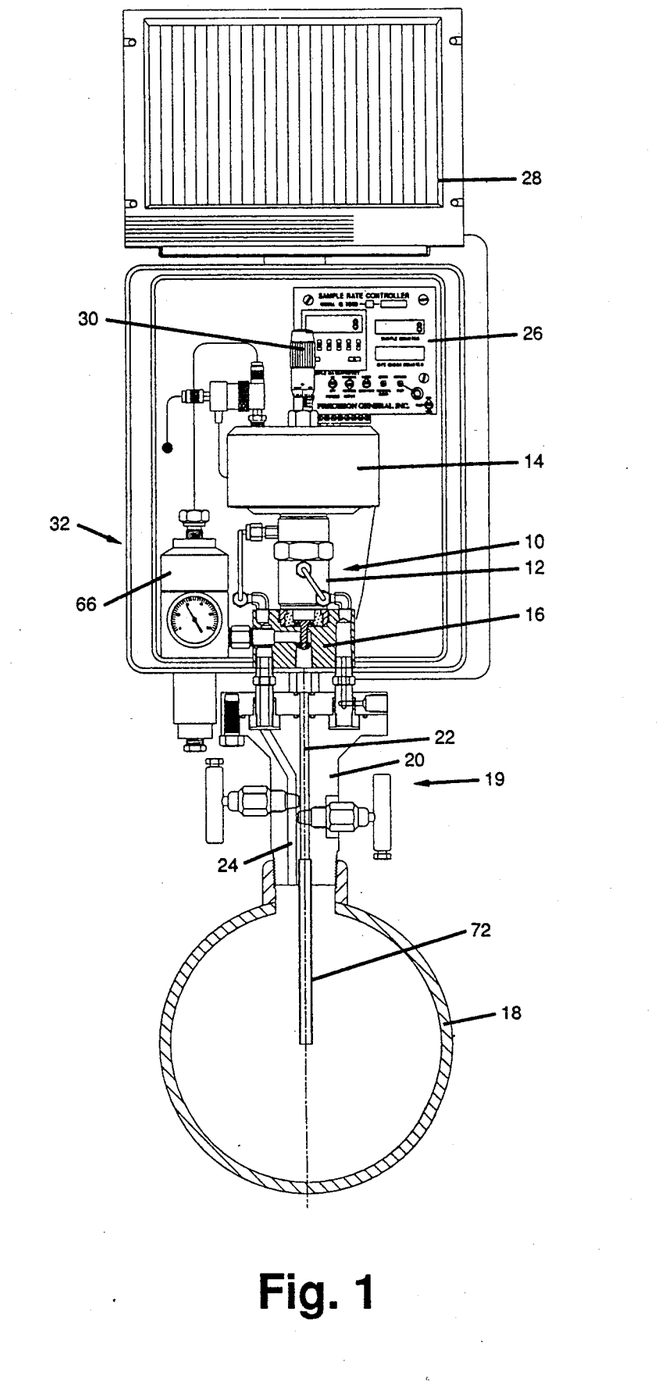
FIG. 1 is a pictorial view, partially in cross-section, of one embodiment of a fluid sampling pump in a typical application directly mounted to a pipeline.

FIG. 1 depicts one embodiment of a sampling pump 10 according to the present invention. The pump 10 consists of a pump housing assembly 12, and a pump driving means or pump operator 14. The embodiment depicted includes a manifold 16 directly connected to the pump housing assembly, and will be discussed further below. The fluid to be sampled by the pump 10 is input to manifold 16 from pipeline 18. Fluid flow through the manifold 16 is nominal compared to fluid flow through the pipeline 18. Moreover, most fluid entering the manifold 16 exits the manifold and returns to line 18. A very small percentage of the fluid passing through the line 18 is pumped by 10 to a sample vessel (not shown) for subsequent analysis.

Fluid flow in the pipeline or other line 18 passes continually in a hot loop through the conduit 72 having its inlet port generally adjacent the center one-third of the pipeline 18, through passageway 22 in the interface body 20, through the pump manifold 16, and then through the return passageway 24 in the interface body 20 and back to the pipeline 18. Fluid continually flows in this hot loop due to the increased fluid pressure in the center of the pipeline 18 compared to the fluid pressure adjacent the sidewalls of the pipeline, where return passageway 24 has its discharge. Some of the hot loop fluid is sampled by the pump 12 in a conventional manner, with the pump operator 14 being controlled by electronic controller 26, which in turn is powered by solar panel module 28. Fluid power to the operator may optionally be supplied by a pressurized air line (not shown), with the level of pressure being controlled by an air regulator. The amount of fluid sampled with each pump stroke may be closely controlled by caliper mechanism 30. The sampled fluid is discharged from the pump and to a sample cylinder or other suitable vessel (not shown). Other details with respect to the sequencing and operation of a sampling pump are disclosed in U.S. Pat. No. 4,531,895, and the previously referenced pending application, both of which are incorporated by reference herein.

As shown in FIG. 1, the pump housing assembly 12, the operator 14, pump manifold 16, controller 26, and regulator 66 are all housed within a single protective housing 32. Housing 32 is typically provided with a conventional hinged door (not shown) for easy access to set or change the settings on the controller 26, and to periodically inspect the components internal of the housing. The solar panel module 28 is secured to and positioned outside the housing 32 to generate electrical power to operate the controller 26. A significant feature of the invention is that the components within the housing 32 need not be discontinued or disassembled in order to directly mount an existing enclosure and internal components to the pipeline. Existing flow lines between the pipeline 18 and the pump manifold 16 may be disconnected, the interface 19 installed as hereinafter explained, and the assembled enclosure, its internal components, and module 28 then mounted as a unit to the pipeline 18.

Figure 2:
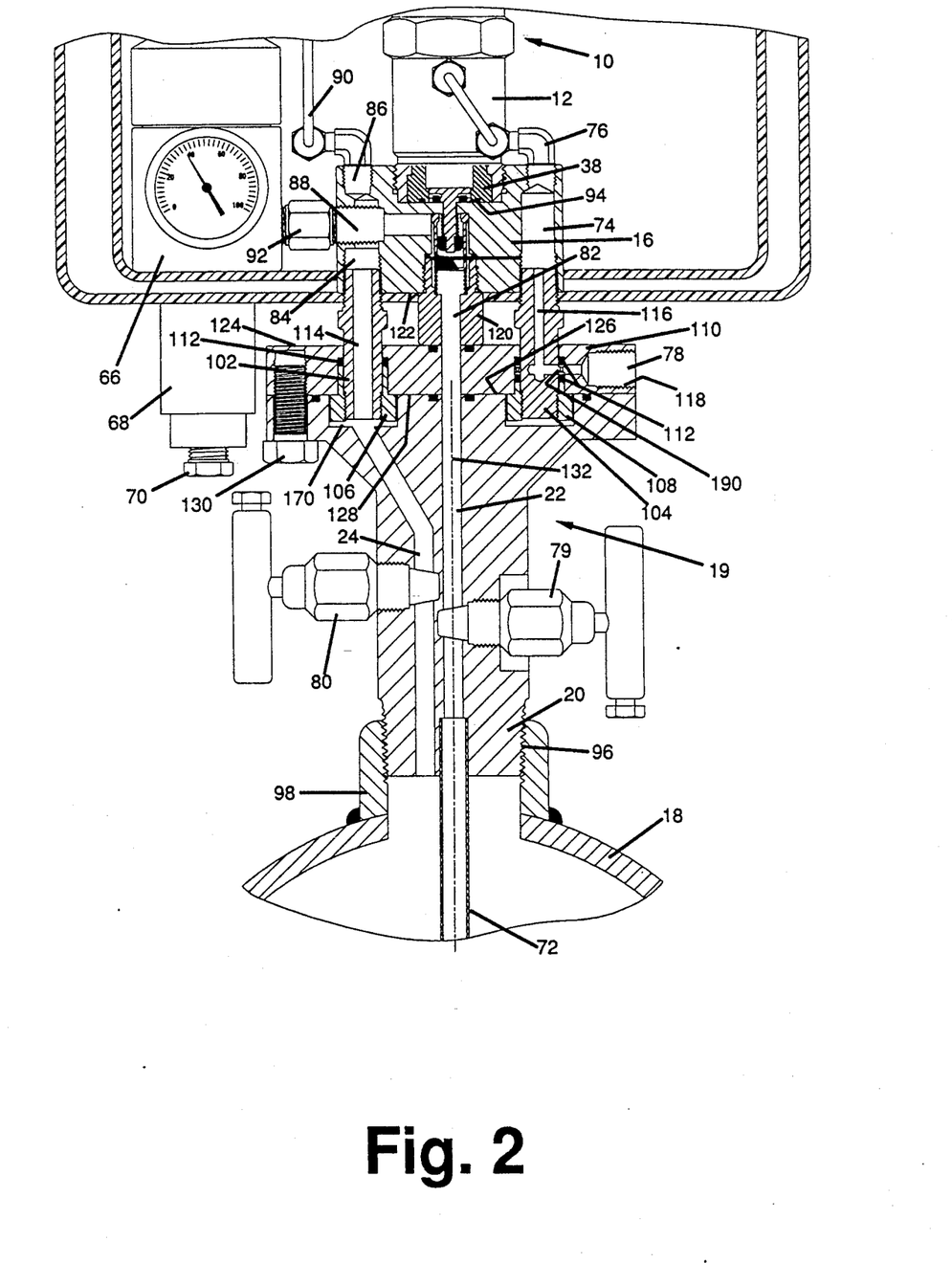
FIG. 2 is a detailed cross-sectional view of a lower portion of a sampling pump and the components of the interface for securing the pump to the pipeline.

FIG. 2 depicts in greater detail the regulator 66, which includes a lower portion 68 and fluid dump plug 70. The lower portion of the body 12 of the sampling pump 10, the interface body 20, and the upper portion of the pipeline 18 and the upper portion of probe tube 72 are also depicted. Interface assembly 19 includes a pair of valve members 79, 80 mounted to the interface body 20 to selectively control fluid flow through the passageways 22, 24, respectively. The lower end of the interface body 22 includes tapered NPT threads 96 for mating with corresponding threads in the nipple 98 secured to the pipeline 18.

Manifold 16 is directly threaded to the pump body. Manifold 16 includes a fluid input port 82 and outlet ports 84, 86 and 88. A small quantity of fluid flows in a hot loop into the manifold 16 via port 82 and out port 84 back to line 18. Port 86 establishes line pressure communication from line 18 to the pump via conduit 90. Line 92 is connected to port 88, and optionally may extend to the regulator 66 for powering operator 14. Seal 94 maintains fluid-tight communication between the lower sleeve segment 38 of the pump 10 and the manifold 16. By directly connecting the manifold to the pump body, the number of leak points may be reduced. The manifold desirably positions the "slip stream" of fluid continually flowing in the hot loop through the manifold to pass in close proximity to the fluid inlet to the sampling pump body. Use of the manifold 16 between the line 18 and the pump body minimizes installation costs, and provides a compact assembly with a fixed hot loop path closely adjacent the pump inlet. Manifold cavity 74 connects to the outlet port in the pump body via conduit 76, and to a sample vessel (not shown) via a conduit connected to port 78, thereby providing a flow path from the pump to the sample vessel. A purge valve line (not shown) within the manifold 16 may be provided, as disclosed is pending application Ser. No. 07/496,368. A cup-shaped strainer in the hot loop line may also enclose the pump inlet valve assembly, as disclosed in the referenced pending application.

The interface 19 includes a pair of similar nipples 102, 104 with threads at each end, with the upper thread being in fluid-tight engagement with ports 84, 74 in the manifold 16, respectively. The lower threads of the fitting 102 is in fluid-tight engagement with fitting 106, and the lower thread of 104 is similarly threaded into engagement with fitting 108. The nipples pass through the plate 110, and a fluid-tight seal is provided between each fitting 106, 108 and the plate 110 by conventional O-rings 112. The nipple 102 includes a through passage 114 for maintaining fluid communication between the port 84 and the passageway 24 in the interface body, and the nipple 104 includes the L-shaped passage 116 for maintaining fluid engagement between the port 74 in the pump manifold 16 and the port 78 in the plate 110. The plate includes tapered threads 118 in port 78 for receiving a line connection (not shown) to the sample container. A spacer nipple 120 is threaded at one end to the manifold 16 and sealed by a conventional O-ring to the face 122 of the pump manifold 16, and another O-ring maintains a fluid tight seal between the upper face 124 of the plate 110 and the lower planar face of the spacer nipple 120. The upper face 126 of the interface body 20 is similarly sealed with the lower face 128 of the plate 110, and a plurality of circumferentially spaced bolts 130 structurally connect the plate 110 and the body 20. Preferably each of the interfaces 122, 124, 126 and 128 is perpendicular to the central axis 132 of the body 20, which is coaxial with the axis of the conduit 72 and also the entry port 82 in the manifold 16.

Figure 3:
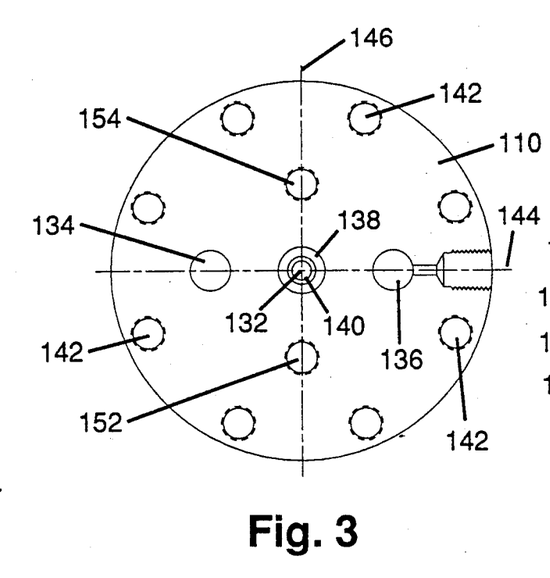
FIG. 3 is a top view of the interface plate generally shown in FIG. 2.

FIG. 3 depicts a top view of a plate 110 shown in FIG. 2, with the drilled ports 134, 136 for receiving the nipples 102, 104, respectively. An annular groove 138 is provided for the O-ring to seal the spacer nipple 120, and the passageway 140 formed about axis 132 provides communication between passage 22 in body 20 and the flow passageway in the spacer nipple 120. A plurality of circumferentially spaced threaded cavities are provided in the lower end of the plate for receiving the respective bolts 130.

Figure 4:
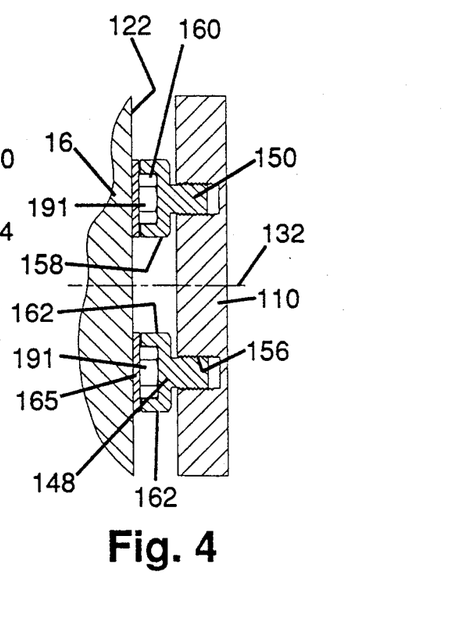
FIG. 4 is a cross-sectional view of the plate shown in FIG. 3, and also illustrating the special bolts for securing the position of the plate with respect to the pump manifold.

FIG. 3 illustrates that the axes of ports 134, 136 are provided within a plane 144 passing through the axis 132. The nipples 102, 104 and the corresponding fittings 106, 108 provide substantial structural support between the pump manifold body 16 and the interface body 20, since these components are spaced substantially from and an opposing sides of the axis 132. These components thus provide substantial structural integrity to resist forces which may be applied between the pump 10 and the interface 19 in the direction of plane 144. In order to provide structural support in the direction of the opposing plane 146 perpendicular to the plane 144 and also passing through the axis 132, a pair of special bolts 148, 150, as shown in FIG. 4, are provided, with the bolts being threaded to the cavities 152, 154 in the top of the plate 110. The cavities 152, 154 are thus not shown in FIG. 2, extend from the top rather than the bottom of the plate 110, and like cavities 142 do not pass through the plate. The axes of cavities 152, 154 are thus within the plane 146, so that the special bolts 148, 150 provide structural support to resist forces which may be applied in the direction of plane 146.

FIG. 4 depicts a cross-sectional view of a lower portion of the enclosure having face 122, the plate 110, and the special bolts 148, 150 discussed above. The spacer nipple 120, the O-ring seals, and the port 82 in manifold 16 are not shown in FIG. 4 for clarity of the depicted components. Each of the bolts includes a straight (not tapered) thread 156 for threaded engagement with similar threads in the plate 110, and head portion 158 having a recess 160 which engages the bottom of the hex head manifold mounting bolts 191. The outer surfaces 162 of the head portion 158 have planar sides for receiving a conventional wrench to facilitate tightening of the bolts to the plate 110. A washer is provided between the heads of each bolt 191 and the manifold 16. The special bolts 148, 150, like the nipples 102, 104, are spaced substantially from the axis 132 to provide the desired structural integrity for the mounting system.

Figure 5:
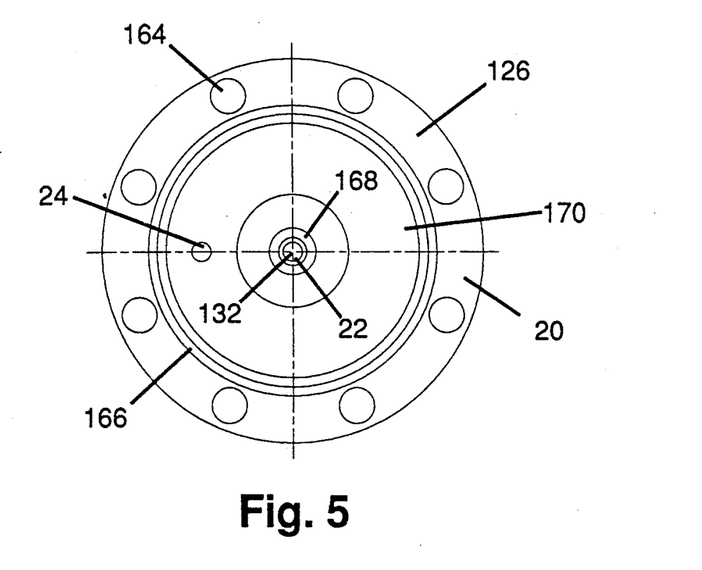
FIG. 5 is a top view of the interface body on FIG. 2.

FIG. 5 illustrates the top view of the interface body 20, which includes the planar upper surface 126 for engagement with the plate 110. The cylindrical ports 164 are provided for receiving the bolts 130, and annular grooves 166 and 168 are formed in the body 20 to receive O-rings for sealing between the plate and the body. The passageway 22 is shown about the axis 132. As explained subsequently, the fittings 106, 108 may rotate with respect to the body 20 prior to assembly, and accordingly an annular groove 170 is provided to accommodate the head portions of the fittings 106, 108 during this rotation. The passageway 24 is thus in fluid communication with the groove 170, so that passageway 114 in nipple 102 is in fluid communication with passageway 24 regardless of the rotational position of the fittings 106 and 108 with respect to the body 20. Referring again to FIG. 2, it should be understood that nipple 104 seals with manifold 16, and thus the rotational position of the horizontal leg of flow passageway 116 is variable when this seal is made up. So that 116 remains in fluid engagement with port 78, an upper and a lower O-ring seal 112 are provided, with the spacing between the seals maintained by the ring-shaped spacer 190 which permits fluid flow out 116 and to port 78. The fitting 108 is thus sealed with the plate 110 so that fluid cannot escape from groove 170. The lower end of nipple 104 does not include a fluid passageway, and accordingly fluid cannot pass directly from groove 170 to passageway 116.

The procedure for installing a sampling system as shown in FIG. 1 will now be described. For ease of explanation, it will be assumed that the regulator, sampling pump, pump manifold, controller and solar module are mounted within the housing 32, since this "package" of components is commercially available from Precision General, Inc. in Houston, TX. In a new installation, the body 20 may be threaded to the pipeline nipple 98. In a retrofit of an existing system, the flow lines between this package and the pipeline nipple may be disconnected, and the package removed from its support stand and set aside.

The tapered thread 96 on the interface body 20 will achieve the desired installation torque at an undetermined rotational position. The operator need not undertorque or overtorque the rotation of the body 20, since the package may subsequently be rotated to a desired position with respect to the body 20. After installing the body 20 (including valves 79, 80), the nipples 102, 104 and the spacer nipple 120 may be threaded to their respective ports in the pump manifold, as shown. Plate 110 may be positioned over the nipples 102, 104 extending from the enclosure 32, and the fittings 106, 108 threaded onto the nipples 102, 104, along with the respective O-rings to hold the plate in position. At this stage, the combination of the plate 110 and the enclosure 32 may be rotated to a preferred position, with cavities 142 in the plate positioned over ports 164 in the body 20. Each of the securing bolts 130 can then be threaded to fix the position of the plate 110 and the components within the enclosure 32 with respect to the body 20. Finally, the special bolts 148, 150 (which were previously threaded to the top of the plate within their respective cavities) may be threaded to move both heads upward until the heads of the bolts engage the bottom surface of the pump manifold mounting bolts 191. These special bolts may then be torqued in a jackscrew manner to achieve the structural integrity desired.

Various modifications will be suggested from the foregoing disclosure. For example, although the annulus 170 in the interface body 20 is preferably sized to both transmit fluid pressure from passageway 114 to passageway 24 regardless of their rotational positions, and to allow the heads of the fittings 106, 108 to rotate within the annulus, an annulus with a smaller cross-sectional area could be provided for fluid passage, and a plurality of recesses drilled in the top of body 20 at regularly spaced intervals for receiving a respective fitting head once the pump has been properly rotated with respect to the interface body. Straight threads may additionally be provided on the body 20 so that a nut and stabilizer foot could be used to increase the structural integrity of the interface body to the pipeline 18. The nut and stabilizer foot may be similar to those described in U.S. Pat. No. 4,920,626 incorporated by reference herein. A modified pump manifold other than the embodiment described herein could be employed, and the interface would be altered to accommodate the different pump manifold.

Standard materials may be used to fabricate the components for the sampling pump and the interface according to the present invention. Most components may be machined from aluminum, steel, or stainless steel, depending on the properties of the fluids intended to pass through the interface and to the pump. The O-rings may be fabricated from various elastomeric materials, such as nylon, Delrin, or PEEK.

The disclosure and description of the invention are thus illustrative and explanatory thereof, and various other changes in the size, shape, and materials, as well as the details of the illustrated construction and the method of assembly, may be made within the scope of the appended claims and without departing from the spirit of the invention.

What is claimed is:

1. An interface for mounting a sampling pump to a flow line having a sampling nipple secured thereto, the sampling pump including a pump manifold having a hot loop passageway with a first hot loop entry port, a second hot loop exit port, and a third port spaced opposite the second port with respect to the first port, each of the first, second, and third ports passing through a lower face of the pump manifold, and the pump having an inlet along the hot loop passageway in the pump manifold, the interface comprising:

an interface body having (a) a hot loop entry passageway through the interface body for maintaining fluid communication between the flow line and the first hot loop entry port, (b) a hot loop return passage through the interface body for maintaining fluid communication between the second hot loop exit port and the flow line, and (c) tapered external threads on an end of the interface body for sealing engagement with mating threads on the sampling nipple;

first and second fittings;

first and second nipples each having an upper end for sealing engagement with the second hot loop exit port and the third port in the pump manifold, respectively, and a lower end for engagement with a corresponding one of the first and second fitting;

a spacer nipple having an upper end for sealing engagement with the first hot loop entry port and a through passageway an interface plate having first and second passageways for receiving portions of the first and second nipples, respectively, and a flow passageway spaced between the first and second passageway for transmitting fluid from the hot loop entry passageway in the interface body to the first hot loop entry port; and connection means for fixedly securing the interface plate to the interface body, such that the pump is directly supported by the interface to the flow line.

2. An interface as defined in claim 1, further comprising:

the third port in the pump manifold transmitting fluid from the sampling pump;

the upper end of the first and second nipples each having threads for engagement with threads of the first and third ports, respectively;

the interface plate including a sample fluid discharge port for transmitting fluid from the sampling pump; and the second nipple including a fluid passageway for maintaining fluid communication between the third port in the pump manifold and the sample fluid discharge port in the interface plate.

3. The interface as defined in claim 1, further comprising:

the first nipple having a flow path therethrough: and the interface body including an annular groove for maintaining fluid communication between the hot loop return passageway in the interface body and the flow path in first nipple, such that rotation of the pump with respect to the interface body may be selected after the interface body is sealingly threaded to the flow line nipple.

4. The interface as defined in claim 3, wherein the annulus in the interface body is sized to accommodate rotation of the first and second fittings each in sealed engagement with the interface plate.

5. The interface as defined in claim 1, further comprising:

the first and second passageways in the interface plate each spaced from and on opposing sides of the flow passageway in the interface plate; and first and second bolts for threading engagement with the corresponding cavities in the interface plate and having a head portion for engagement with the pump manifold.

6. The interface as defined in claim 5, further comprising:

the first and second nipples being spaced from and on opposing sides of the flow passageway in the interface plate, the nipples having corresponding first and second nipple axes defining a first plane; and the first and second bolts each having a corresponding first and second axis defining a second plane substantially perpendicular to the first plane.

7. The interface as defined in claim 1, further comprising:

a first valve for controlling fluid flow through the hot loop entry passageway through the interface body; and a second valve for controlling fluid flow through the hot loop return passageway in the interface body.

8. The interface as defined in claim 1, further comprising:

an enclosure; and the sampling pump is mounted within the enclosure such that the sampling pump within the enclosure may be mounted to the flow line via the interface without disconnecting or removing the pump from the enclosure.

9. A sampling pump and interface apparatus for mounting the sampling pump to a flow line having a sampling nipple secured thereto, the apparatus comprising:

the sampling pump including a pump manifold having a hot loop passageway with a first hot loop entry port, a second hot loop exit port, and a third port spaced opposite the second port with respect to the first port for transmitting fluid from the sampling pump, each of the first, second, and third port passing through a lower face of the pump manifold, the pump having an inlet along the hot loop passageway in the pump manifold, and a inlet valve assembly for controlling fluid flow from the hot loop passageway in the pump manifold into the pump; and the interface including (a) an interface body having a hot loop entry passageway for maintaining communication between the flow line and the first hot loop entry port, a hot loop return passageway for maintaining fluid communication between the second hot loop exit port and the flow line, and a tapered thread at a lower end of the interface body for sealing engagement with mating threads on the sampling nipple, (b) first and second fittings, (c) first and second nipples each having an upper end for sealing engagement with the second hot loop exit port and the third port in the pump manifold, respectively, and threaded lower end for engagement with a corresponding one of the first and second fitting, (d) an interface plate having first and second passageways for receiving portions of the first and second nipples, respectively, and a flow passageway spaced between the first and second passageways for transmitting fluid from the hot loop entry passageway in the interface body to the first hot loop entry port, (e) a spacer nipple having an upper end for sealing engagement with the first hot loop entry port and a lower end in fluid communication with the hot loop entry passageway in the interface body, and (f) securing means for fixing the position of the interface plate with respect to the interface body such that the pump and pump manifold may be mounted directly to the flow line by the interface.

10. The apparatus as defined in claim 9, further comprising:
the upper end of the first and second nipples each having threads for engagement with threads of the first and third ports, respectively;
the interface plate including a sample fluid discharge port for transmitting fluid from the sampling pump; and
the second nipple including a fluid passageway for maintaining fluid communication between the third port in the pump manifold and the sample fluid discharge port in the interface plate.

11. The apparatus as defined in claim 9, further comprising:
the first nipple having a flow path therethrough; and
the interface body including an annular groove for maintaining fluid communication between the not loop return passageway in the interface body and the flow path in first nipple, such that rotation of the pump with respect to the interface body may be selected after the interface body is sealingly threaded to the flow line nipple.

12. The apparatus as defined in claim 9, further comprising:
first and second cavities in the interface plate each spaced from and on opposing sides of the flow passageway in the interface plate; and
first and second bolts for threading engagement with the corresponding cavities in the interface plate and having a head portion for engagement with the pump manifold.

13. The apparatus as defined in claim 12, further comprising:
the first and second nipples being spaced from and on opposing sides of the flow passageway in the interface plate, the nipples having corresponding first and second nipple defining a first plane; and
the first and second bolts each having a corresponding first and second axis defining a second plane substantially perpendicular to the first plane.

14. The apparatus as defined in claim 9, further comprising:
an enclosure; and
the sampling pump is mounted within the enclosure such that and the sampling pump within the enclosure may be mounted to the flow line via the interface without disconnecting or removing the pump from the enclosure.

15. A method of interconnecting a sampling pump to a flow line having a sampling nipple secured thereto, the sampling pump including a pump manifold having a hot loop passageway with a first hot loop entry port, a second hot loop exit port, and a third port spaced opposite the second port with respect to the first port and transmitting fluid from the pump to a container, with the first, second and third ports passing through a lower face in the pump manifold, and a pump inlet along the hot loop passageway in the pump manifold, the method comprising:
forming an interface body having (a) a hot loop entry passageway therethrough, (b) a hot loop return passageway therethrough, (c) tapered threads at a lower end of the interface body:
forming first and second nipples;
forming a spacer nipple:
forming an interface plate having first and second passageways and a flow passageway spaced between the first and second passageways;
threading the interface body to the sampling nipple to obtain sealing engagement between the interface body and the sampling nipple;
interconnecting each of the first and second nipples to the second and third ports in the pump manifold, respectively;
interconnecting the spacer nipple to the first port in the pump manifold;
placing the plate over exposed ends of the first and second nipples such that the nipples pass through the respective first and second passageways in the plate;
sealing each of the first and second nipples with the plate;
thereafter rotating the plate and the pump as an assembly with respect to the interface body so that the pump has a desired rotational position; and
thereafter fixing the position of the plate with respect to the interface body.

16. The method as defined in claim 15, further comprising:
forming an annular groove in the interface body for maintaining fluid communication between the not loop return passageway in the interface body and a flow path through the first nipple, such that the rotational position of the pump with respect to the interface body may be selected after the interface body is sealed to the flow line nipple.

17. The method as defined in claim 15, further comprising:
providing an enclosure;
mounting the pump within the enclosure; and
thereafter passing the first and second nipples through the enclosure and into engagement with the second and third ports in the pump manifold, respectively.

18. The method as defined in claim 17, wherein the enclosure and the sampling group and the pump manifold mounted within the enclosure are mounted to and supported by the flow line solely by the interface.

* * * * *

UNITED STATES PATENT AND TRADEMARK OFFICE
CERTIFICATE OF CORRECTION

PATENT NO. : 5,109,709

DATED : May 5, 1992

INVENTOR(S) : Spencer Nimberger

It is certified that error appears in the above-identified patent and that said Letters Patent is hereby corrected as shown below:

In Column 11, line 56, change "not" to --hot--.

In Column 14, line 4, change "group" to --pump--.

Signed and Sealed this

Third Day of August, 1993

Attest:

MICHAEL K. KIRK

*Attesting Officer*    Acting Commissioner of Patents and Trademarks